United States Patent
Jones et al.

(10) Patent No.: US 9,902,673 B2
(45) Date of Patent: Feb. 27, 2018

(54) METHODS FOR PRODUCING BUTANOL

(71) Applicants: William D. Jones, Rochester, NY (US); Sumit Chakraborty, Rochester, NY (US)

(72) Inventors: William D. Jones, Rochester, NY (US); Sumit Chakraborty, Rochester, NY (US)

(73) Assignee: The University of Rochester, Rochester, NY (US)

( * ) Notice: Subject to any disclaimer, the term of this patent is extended or adjusted under 35 U.S.C. 154(b) by 0 days.

(21) Appl. No.: 15/211,393

(22) Filed: Jul. 15, 2016

(65) Prior Publication Data

US 2017/0015610 A1   Jan. 19, 2017

Related U.S. Application Data

(60) Provisional application No. 62/193,294, filed on Jul. 16, 2015.

(51) Int. Cl.
| | | |
|---|---|---|
| *C07C 29/34* | (2006.01) | |
| *B01J 31/22* | (2006.01) | |
| *B01J 23/755* | (2006.01) | |
| *B01J 23/72* | (2006.01) | |
| *B01J 31/20* | (2006.01) | |

(52) U.S. Cl.
CPC ............... *C07C 29/34* (2013.01); *B01J 23/72* (2013.01); *B01J 23/755* (2013.01); *B01J 31/20* (2013.01); *B01J 31/2295* (2013.01); *B01J 2231/40* (2013.01); *B01J 2531/821* (2013.01); *B01J 2531/827* (2013.01)

(58) Field of Classification Search
CPC ......... C07C 29/34; B01J 23/72; B01J 23/755; B01J 31/20; B01J 31/2295; B01J 2231/40; B01J 2531/821; B01J 2531/827; B01J 23/468; B01J 35/0006
See application file for complete search history.

(56) References Cited

U.S. PATENT DOCUMENTS

| | | | |
|---|---|---|---|
| 8,318,989 B2 | 11/2012 | Kourtakis et al. | |
| 8,779,216 B2 | 7/2014 | Wick et al. | |
| 2014/0179958 A1* | 6/2014 | Zhang | C07C 29/34 568/905 |

FOREIGN PATENT DOCUMENTS

JP          2008266267    *  6/2008

OTHER PUBLICATIONS

English Translation of JP2008266267, Nov. 6, 2008, pp. 1-10.*
Atsumi, et al., "Metabolic engineering of *Escherichia coli* for 1-butanol production", Metabolic Eng. 10, 2008, 305-311.
Black, et al., "Borrowing Hydrogen: Indirect "Wittig" Olefination for the Formation of C—C Bonds from Alcohols", Eur. J. Org. Chem., 2006, 4367-4378.
Carlini, et al., "Selective synthesis of isobutanol by means of the Guerbet reaction Part 2. Reaction of methanol/ethanol and methanol/ethanol/n-propanol mixtures over copper based/MeONa catalytic systems", J. Mol. Catal. A: Chem. 200, 2003, 137-146.
Chakraborty, et al., "Well-Defined Iron Catalysts for the Acceptorless Reversible Dehydrogenation—Hydrogenation of Alcohols and Ketones", ACS Catal. 4, 2014, 3994-4003.
Chakraborty, et al. "Highly Selective Formation of n-Butanol from Ethanol through the Guerbet Process: A Tandem Catalytic Approach", J Am. Chem. Soc. 137, 2015, 14264-14267.
Degering, et al., "Polymerization of acetaldehyde and crotonaldehyde catalyzed by aliphatic tertiary amines", J. Polym. Sci. 7, 1951, 653-656.
Dowson, et al., "Catalytic Conversion of Ethanol into an Advanced Biofuel: Unprecedented Selectivity for n-Butanol," Angew. Chem., Int. Ed 52, 2013, 9005-9008.
Durre, "Biobutanol: An attractive biofuel", Biotcehnol. J. 2, 2007, 1525-1534.
Edwards, et al., "Borrowing hydrogen: a catalytic route to C—C bond formation from alcohols", Chem. Commun 1, 2004, 90-91.
Fortman, et al., "A Versatile Cuprous Synthon: [Cu(IPr)(OH)] (IPr = 1,3 bis(diisopropylphenyl)imidazol-2-ylidene)", Organometallics 29, 2010, 3966-3972.
Fujita, et al., "Dehydrogenative Oxidation of Primary and Secondary Alcohols Catalyzed by a Cp Ir Complex Having a Functional C,N-Chelate Ligand", Org. Lett. 13, 2011, 2278-2281.
Fujita, et al., "Homogeneous Perdehydrogenation and Perhydrogenation of Fused Bicyclic N-Heterocycles Catalyzed by Iridium Complexes Bearing a Functional Bipyridonate Ligand" J. Am. Chem. Soc. 136, 2014, 4829-4832.
Fujisawa et al., "Structural and spectroscopic comparison of five-coordinate cobalt(II) and nickel(II) thiolato complexes with the related four-coordinate complexes", Sci Direct. 361, 2008, 1134-1141.
Furukawa, et al., "High Polymerization of Acetaldehyde by Alumina—A New Method of Preparation of Polyether", J. Polym. Sci 36, 1959, 546.
Green, "Fermentative production of butanol—the industrial perspective", Curr. Opin. Biotechnol. 22, 2011, 7 pages.
Guerbet, "Action of ethyl, isobutyl, isoamyl alcohols on their sodium derivatives", Acad. Sci. Paris 128, 1899, 1002-1004.
Guerbet, "Condensation of isopropyl alcohol with its sodium derivative; formation of methyl isobutyl carbinol and 2.4-dimethyl-6-heptanol", Acad. Sci. Paris 149, 1909, 129-132.
Harvey, et al., "The role of butanol in the development of sustainable fuel technologies", J. Chem. Technol. Biotechnol. 86, 2011, 2-9.

(Continued)

*Primary Examiner* — Pancham Bakshi
*Assistant Examiner* — Mark R Luderer
(74) *Attorney, Agent, or Firm* — Meunier Carlin & Curfman LLC

(57) ABSTRACT

Methods and compositions for producing 1-butanol are described herein. In some examples, the methods can comprise, contacting a reactant comprising ethanol with a catalyst system, thereby producing a product comprising 1-butanol. The catalyst system can comprise, for example, an iridium catalyst and a nickel, copper, and/or zinc catalyst. The nickel, copper, and zinc catalysts can comprise nickel, copper, and/or zinc and a sterically bulky ligand.

28 Claims, 2 Drawing Sheets

(56) References Cited

OTHER PUBLICATIONS

Hikichi et al., "Reaction of Hydroxo Complexes of Divalent Metal Ions with Amide", J Chem. Soc. Commun. 1994, 1737-1738.

Hikichi et al., "First Synthesis and Structural Characterization of Dinuclear M(III) Bis(u-oxo) Complexes of Nickel and Cobalt with Hydrotris(pyrazolyl)borate Ligand", J. Am. Chem. Soc. 120, 1998, 10567-10568.

Hikichi et al., Oxygenation of Saturated Hydrocarbyl Groups in the Dinuclear Ni(III) Bis(u-oxo) Complexes with the Hydrotris (pyrazolyl) borate Ligands TpR (R=Me3 and Pri2), Chem Let. 1999, 979-980.

Hikichi et al., "Structural Characterization and Intramolecular Aliphatic CÿH Oxidation Ability of MIII(m-O)2MIII Complexes of Ni and Co with the Hydrotris-(3,5-dialky1-4-X-pyrazolyl)borate Ligands TpMe2,X (X=Me, H, Br) and TpiPr2", Chem.—Eur. J. 723, 2001, 5012-5028.

Hikichi et al., "Structural Characterization and Oxidation Activity of a Nickel(II) Alkylperoxo Complex", Angew. Chem. Int. Ed. 48, 2009, 188-191.

Hikichi et al., "Characterization of nickel(II)-acylperoxo species relevant to catalytic alkane hydroxylation by nickel complex with mCPBA", Dalton Trans. 42, 2013, 3346-3356.

Jin, et al., "Progress in the production and application of n-butanol as a biofuel", Renewable Sustainable Energy Rev. 15, 2011, 4080-4106.

Kitajima et al., "Fixation of Atmospheric CO2 by a Series of Hydroxo Complexes of Divalent Metal Ions and the Implication for the Catalytic Role of Metal Ion in Carbonic Anhydrase", J Am Chem Soc. 115, 1993, 5496-5508.

Koda, "Guerbet Reaction of Ethanol to n-Butanol Catalyzed by Iridium Complexes", Chem. Lett. 38:8, 2009, 838-839.

Kozlowski et al., "Heterogeneous Catalysts for the Guerbet Coupling of Alcohols", Am. Chem. Soc. 2013, 1588-1600.

Kujime et al., "Interaction of hydroperoxopalladium complexes, (TpR)(py)Pd—OOH, with hydroxo-nickel and -cobalt complexes, [(u-OH)(MTpR)]2 (M=Ni, Co), leading to oxidative dehydrogenation of the saturated hydrocarbyl moiety in the ancillary ligand (TpiPr2)", Dalton Trans. 2003 b, 3506-3515.

Kujime et al., "Synthesis and characterization of enolato-cobalt and - nickel complexes bearing TpiPr2 ligand, [TpiPr2M(xchy)]n [TpiPr2=hydrotris(3,5-diisopropylpyrazolyl)borato; n=1,2], obtained from hydroxometal complexes, (u-OH)2(MTpiPr2)2, and active methylene compounds, CH2XY", Inorganica Chimica Acta 350, 2003, 163-174.

Lopez-Banet et al., "Crystal Structures and Magnetic Properties of Nickel Complexes with Hydrotris(pyrazolyl)borate Ligand and Double Bridged by Phosphate Esters", Inorg. Chem.50, 2011, 437-443.

Lopez-Banet et al., "Networks based on hydrogen-bonds containing phosphorus anions and tris(3,5-dimethylpyrazolyl)borate nickel(II) moieties", Polyhedron 31, 2012, 575-586.

Lopez-Banet et al., "Crystal Structures and Spectroscopic and Theoretical Properties of Pentacoordinate Nickel(II) Complexes Containing Tris(pyrazolyl)borate and Quinolinate Ligands", Eur. J. Inorg. Chem. 2013, 4280-4290.

Lopez-Banet et al., "Structure and Spectroscopic Properties of Nickel Benzazolate Complexes with Hydrotris(pyrazolyl)borate Ligand", Inorg. Chem. 53, 2014, 5502-5514.

Lopez-Banet et al., "Blocking and bridging ligands direct the structure and magnetic properties of dimers of pentacoordinate nickel (II)", Dalton Trans .44, 2015, 6839-6847.

Matsu-Ura et al., "Guerbet Reaction of Primary Alcohols Leading to b-alkylated Dimer Alcohols Cata;lyzed by Iridium Complexes", J Org Chem 71:21, 2006, 5 pages.

Matsunaga et al., "Structural and Spectroscopic Characterization of First-Row Transition Metal(II) Substituted Blue Copper Model Complexes with Hydrotris(pyrazolyl)borate", Inorg. Chem. 44, 2005, 325-335.

Nakasawa et al., "Dioxygen Activation and Substrate Oxygenation by a p-Nitrothiophenolatonickel Complex: Unique Effects of an Acetonitrile Solvent and the p-Nitro Group of the Ligand", Inorg. Chem. 50, 2011, 9933-9935.

O'Lenick, "Guerbet Chemistry", Surfactants Deterg. 4, 2001, 311-315.

Pruett, "Hydroformylation", Adv. Organomet. Chem 17, 1979, 1-60.

Ragauskas, et al., "The path forward for biofuels and biomaterials", Science 311, 2006, 484-489.

Riittonen, et al., "One-Pot Liquid-Phase Catalytic Conversion of Ethanol to 1-Butanol over Aluminium Oxide—The Effect of the Active Metal on the Selectivity", Catalysts 2, 2012, 68-84.

Sheehan, et al., "Energy and Environmental Aspects of Using Corn Stover for Fuel Ethanol", J. Ind. Ecol. 7, 2003, 117-146.

Spasyuk, et al., "Replacing Phosphorus with Sulfur for the Efficient Hydrogenation of Esters", Angew. Chem., Int. Ed. 2013, 52, 2538-2542 and reference cited therein.

Sun et al., "Recent Advances in Catalytic Conversion of Ethanol to Chemicals", ACS Catal. 4, 2014, 1078-1090.

Veibel, et al., "On the mechanism of the Guerbet reaction", Tetrahedron 23, 1967, 1723-1733.

Wingad, et al., "Catalytic Conversion of Ethanol to n-Butanol Using Ruthenium P—N Ligand Complexes", ACS Catal. 5, 2015, 5822-5826.

Xu, et al., "Direct self-condensation of bio-alcohols in the aqueous phase", Green Chem. 16, 2014, 3971-3977.

Yamaguchi, et al., "Homogeneous Catalytic System for Reversible Dehydrogenation—Hydrogenation Reactions of Nitrogen Heterocycles with Reversible Interconversion of Catalytic Species", J. Am. Chem. Soc. 131, 2009, 8410-8412.

* cited by examiner

METHODS FOR PRODUCING BUTANOL

CROSS REFERENCE TO RELATED APPLICATIONS

This application claims the benefit of priority to U.S. Provisional Application 62/193,294, filed Jul. 16, 2015, which is incorporated by reference herein in its entirety.

ACKNOWLEDGEMENT OF GOVERNMENT SUPPORT

This invention was made with government support under Grant No. 1205189 awarded by the National Science Foundation. The government has certain rights in the invention.

BACKGROUND

Butanol represents an alternative to gasoline as a transportation fuel with certain advantages over ethanol. For example, butanol can be blended into gasoline at higher concentrations (16%) than ethanol, which can provide more renewable content in every gallon. Butanol can be used in existing vehicles and infrastructure (e.g., a drop-in fuel). Butanol does not mix with water as does ethanol, meaning it can be transported via existing infrastructure. Butanol has a low vapor pressure, so there will be lower evaporative losses associated with butanol compared to ethanol.

In addition, 1-butanol can be used as an entry level chemical in the synthetic commodity chemical industry. Butanol can be used in the chemical industry for different purposes, such as the manufacture of butyl acrylate, butyl acetate, glycols, plasticizers and solvents. Butanol can be used in the manufacture of pharmaceuticals, polymers, pyroxylin plastics, herbicide esters, and butyl xanthate. Butanol can also be used as a solvent for the extraction of essential oils or as an ingredient in perfumes; as an extractant in the manufacture of antibiotics, hormones, and vitamins; as a solvent for paints, coatings, natural resins, gums, synthetic resins, alkaloids, and camphor. Other applications of butanol include, for example, as a swelling agent in textiles; as a component of brake fluids, cleaning formulations, degreasers, and repellents; and as a component of ore floatation agents and of wood-treating systems.

Production of multi-carbon alcohols, such as butanol, using most conventional processes has been limited by economic and environmental constrains. The compositions and methods disclosed herein address these and other needs.

SUMMARY

In accordance with the purposes of the disclosed methods and systems, as embodied and broadly described herein, the disclosed subject matter related to methods for producing 1-butanol and catalyst systems. The methods can comprise, for example, contacting a reactant comprising ethanol with a catalyst system, thereby producing a product comprising 1-butanol. In some examples, the reactant can be contacted with the catalyst system at a temperature of from 100° C. to 500° C. The pressure can be at atmospheric (1 atm) or when in a sealed vessel up to 10 atm. In some examples, the reactant can be contacted with the catalyst system for from 0.01 hours to 100 hours. In some examples, the ethanol conversion can be 30% or more. In some examples, the 1-butanol selectivity can be 80% or more. In some examples, the 1-butanol yield can be 20% or more.

The catalyst system can comprise, for example, an iridium catalyst and a nickel or copper or zinc catalyst. The iridium catalyst, for example, can comprise any iridium catalyst known in the art. In some examples, the iridium catalyst can comprise:

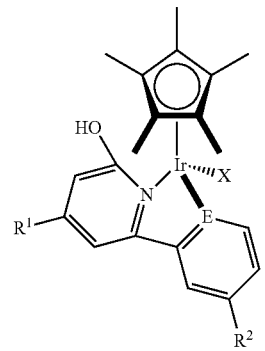

wherein
E is C or N;
X is halogen or other neutral ligand; and
$R^1$ and $R^2$ are independently selected from H, alkyl, alkenyl, cycloalkyl, cycloalkenyl, or aryl. In a specific example, the iridium catalyst can comprise:

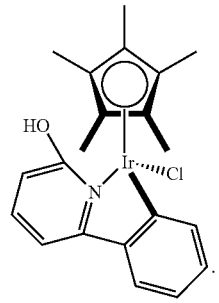

The nickel catalyst can comprise nickel and a sterically bulky ligand. The copper catalyst can comprise copper and a sterically bulky ligand. The zinc catalyst can comprise zinc and a sterically bulky ligand. In some examples, the sterically bulky ligand can comprise a tripodal ligand. Examples of tripodal ligands include, for example, scorpionate ligands. In some examples, the sterically bulky ligand can comprise a substituted or unsubstituted trispyrazoylborate ligand. In some examples, the sterically bulky ligand can comprise a tris(3,5-dimethyl-1-pyrazolyl)borate ligand. In other examples, the sterically bulky ligand can comprise a tris(3,5-diethyl-1-pyrazolyl)borate, tris(3,5-dipropyl-1-pyrazolyl)borate, tris(3,5-diisopropyl-1-pyrazolyl)borate, tris(3,5-dibutyl-1-pyrazolyl)borate, tris(3,5-di(iso, sec, or tert)buty-1-pyrazolyl)borate, or tris(1-pyrazolyl)borate ligand. In still other examples, the pyrazolyl moiety of the tris(1-pyrazolyl)borate ligand can be substituted with one or more substituents chosen from hydrogen, alkyl, alkenyl, cycloalkyl, cycloalkenyl, or aryl. In other examples, the sterically bulky ligand can comprise a substituted aryl, e.g., a di or tri alkyl substituted aryl.

In some examples, the nickel catalyst can comprise:

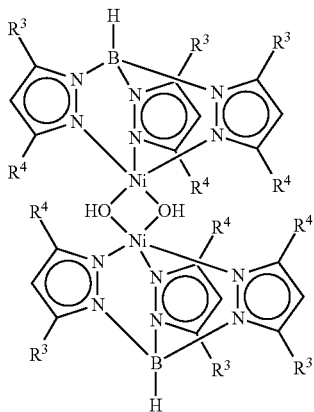

wherein each $R^3$ and $R^4$ are independently selected from H, alkyl, alkenyl, cycloalkyl, cycloalkenyl, or aryl. In a specific example, the nickel catalyst can comprise:

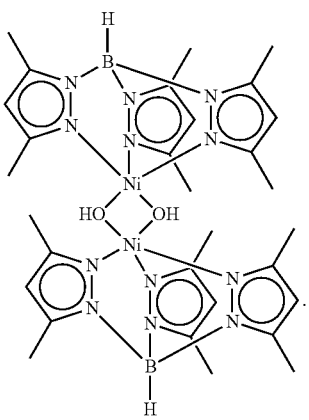

In some examples, the catalyst can comprise:

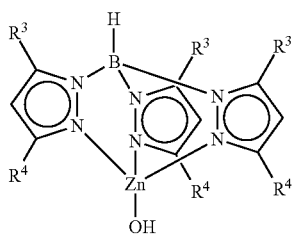

wherein each $R^3$ and $R^4$ are independently selected from H, alkyl, alkenyl, cycloalkyl, cycloalkenyl, and aryl. In specific examples, each $R^3$ and $R^4$ are independently selected from methyl, ethyl, propyl (e.g., iso-propyl), and butyl (e.g., sec-butyl or tert-buty).

In a specific example, the nickel, copper, or zinc catalyst can comprise:

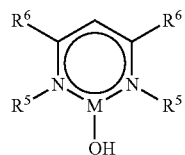

wherein M is Ni, Cu, or Zn; and $R^5$ and $R^6$ are independently selected from H, alkyl, alkenyl, cycloalkyl, cycloalkenyl, and aryl. In specific examples, each $R^5$ and $R^6$ are independently selected from methyl, ethyl, propyl (e.g., iso-propyl), and butyl (e.g., sec-butyl or tert-buty). In specific examples, $R^5$ and/or $R^6$ are independently selected from di- and tri-alkyl substituted aryl, e.g., aryl with two or three methyl, ethyl, propyl (e.g., iso-propyl), or butyl (e.g., sec-butyl or tert-buty) groups.

In a specific example, the copper catalyst can comprise:

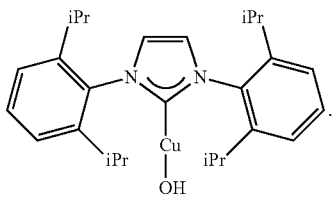

In the disclosed methods, the reactions can take place in the present of a base, e.g., NaOMe, NaOEt, NaOBu, KOH, NaOH, and the like.

Also disclosed herein are catalyst systems comprising an iridium catalyst and a nickel catalyst, wherein the nickel catalyst comprises nickel and a sterically bulky ligand.

Additional advantages will be set forth in part in the description that follows or may be learned by practice of the aspects described below. The advantages described below will be realized and attained by elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
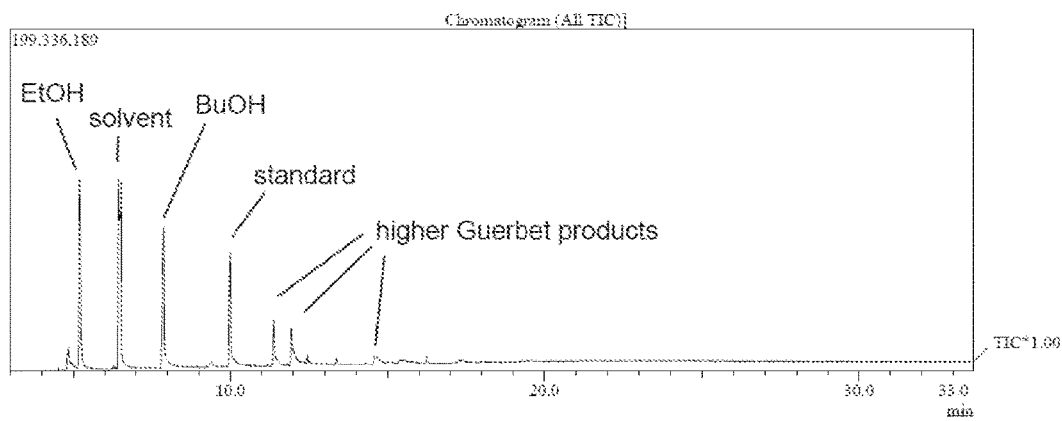
FIG. 1 displays the gas chromatograph of the results of a Guerbet process for the production of butanol from ethanol using an iridium compound and potassium hydroxide as catalysts.
Figure 2:
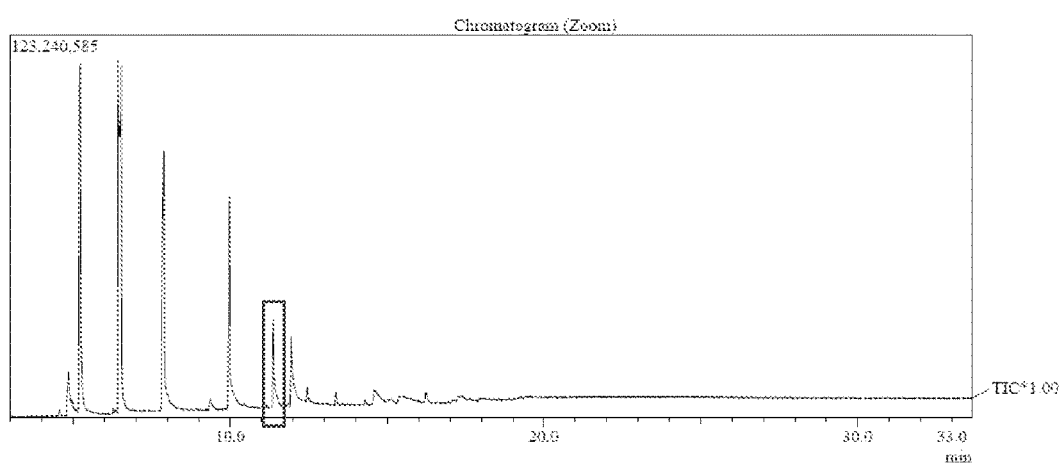
FIG. 2 displays a zoomed in version of the gas chromatograph from FIG. 1, with the boxed in peak selected for mass spectrometry.
Figure 3:
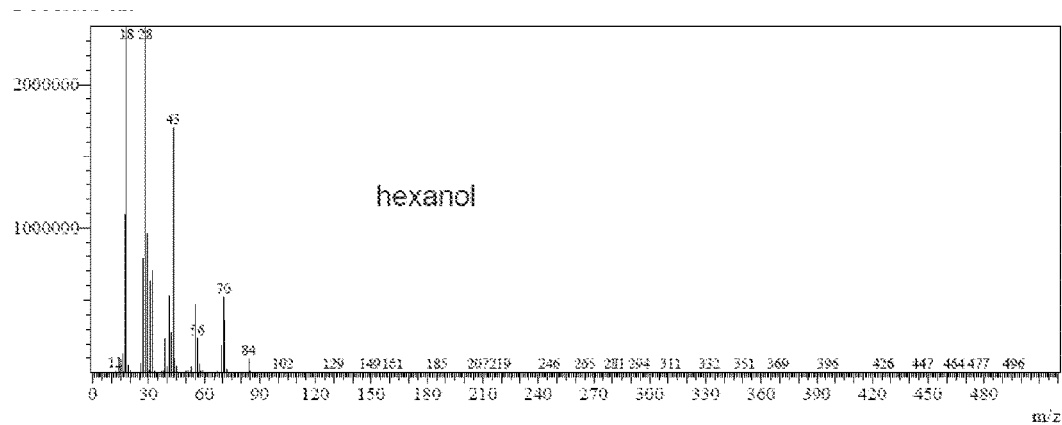
FIG. 3 displays the mass spectrum of the indicated peak from FIG. 2, which was identified as hexanol.
Figure 4:
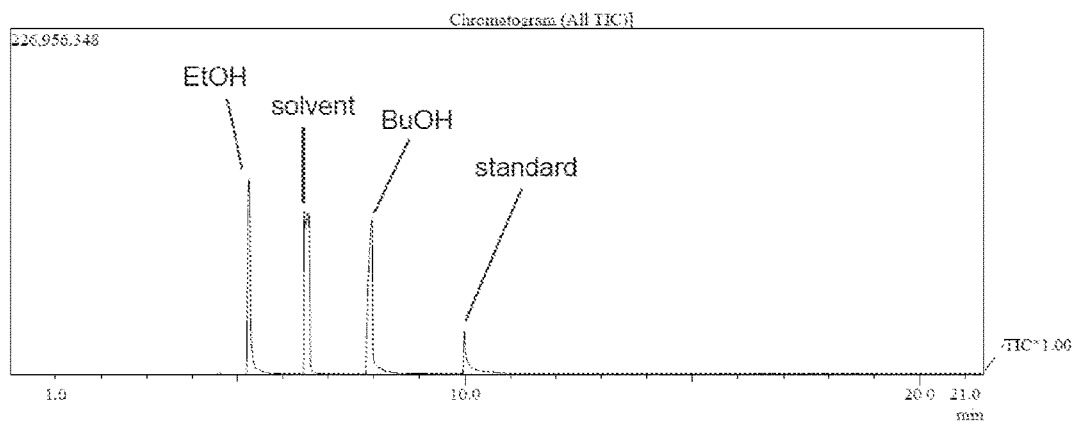
FIG. 4 displays the gas chromatograph of the results of a Guerbet process for the production of butanol from ethanol using an iridium catalyst and a nickel catalyst.
Figure 5:
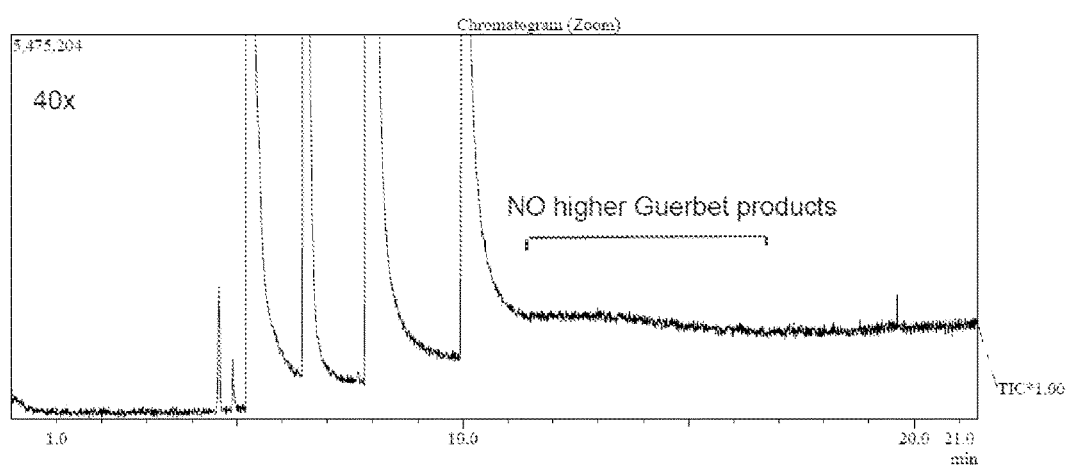
FIG. 5 displays a zoomed in version of the gas chromatograph from FIG. 4, indicating the lack of peaks for higher Guerbet products.
Figure 6:
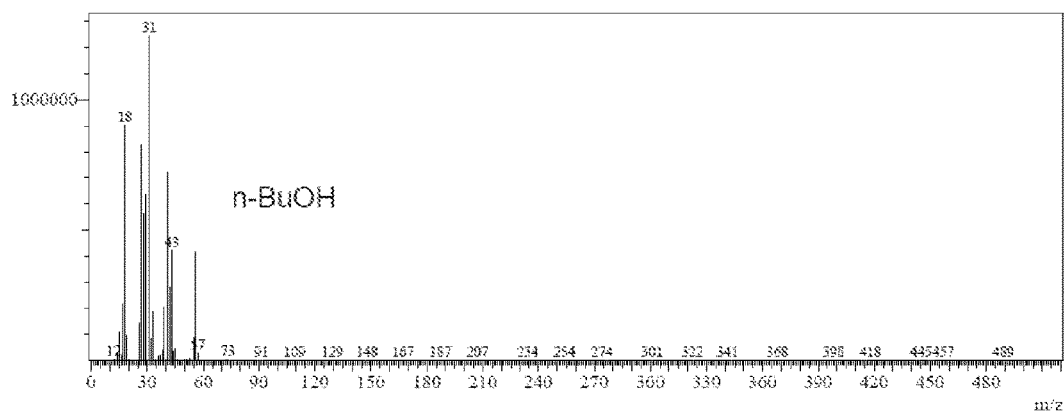
FIG. 6 displays the mass spectrum of the butanol peak from FIG. 4.

The methods and systems described herein may be understood more readily by reference to the following detailed description of specific aspects of the disclosed subject matter and the Examples included therein.

Before the present methods and systems are disclosed and described, it is to be understood that the aspects described below are not limited to specific methods or specific systems, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Butanol represents an alternative to gasoline as a transportation fuel with many desirable properties. In addition, 1-butanol can be used as an entry level chemical in the synthetic commodity chemical industry.

Two examples of current practices for making butanol are shown in Scheme 1. The first of these produces the isomer isobutanol by fermentation of sugars (e.g., with clostridium acetobutylicum in the ABE process) from organic material (e.g., biomass) including, for example, corn, wheat, sugarcane, woody mass, and non-food plants (e.g., algal oils). The second route is sometimes referred to as the petrochemical 'oxo' process. The 'oxo' process involves the hydroformylation of propene (e.g., propene reacts with synthesis gas, such as CO and $H_2$) to form butylaldehyde, which can subsequently be hydrogenated to produce butanol. This route produces a mixture of 1-butanol and isobutanol. It also requires carbon monoxide, hydrogen and propene as feedstocks, limiting the cost of butanol via this process (Pruett R L. *Adv. Organomet. Chem.* 1979, 17, 1). The starting propene can be obtained, for example, from naphtha cracking or the dehydrogenation of propane.

Scheme 1. Established routes to butanol.

Fermentation:

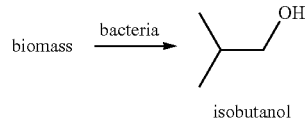

isobutanol

Hydroforymlation/hydrogenation:

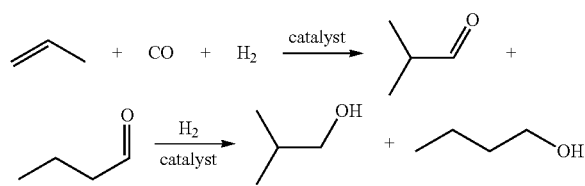

One of the best known processes for the production of multi-carbon alcohols, such as butanol, is the Guerbet reaction (Guerbet M. *C. R. Acad. Sci. Paris.* 1899, 128, 1002; O'Lenick Jr. A J. *Surfactants Deterg.* 2001, 4, 311). In the conventional Guerbet reaction, a primary or secondary alcohol can be converted to a primary alcohol of about twice the molecular weight, which is alkylated in the beta position to the carbon atom bearing the OH group.

The reaction mechanism for the preparation of butanol by condensation from ethanol via the Guerbet reaction is shown in Scheme 2. In the first step (step A), ethanol (R=H) is oxidized (e.g., dehydrogenated) to an intermediate aldehyde, acetaldehyde. In the second step (step B), two of the intermediate aldehydes (e.g., two acetaldehydes) undergo an aldol condensation, producing the butenal (also known as crotonaldehyde) and water. The butenal is then reduced to butanol via hydrogenation with the hydrogen from the first step (step C).

Scheme 2. Guerbet process.

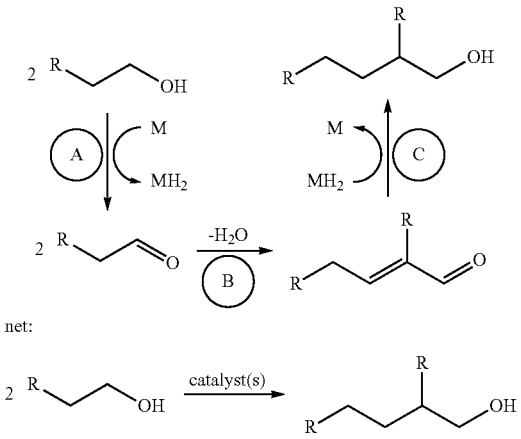

In some examples, the Guerbet process can suffer from poor selectivity. The condensation product formed (e.g., butanol) can undergo further aldol reactions with itself and/or with any starting alcohol (e.g., ethanol) still present in the reaction mixture, which can lead to a series of further alcohols (e.g., branched or linear alcohols) with higher molecular weights (e.g., hexanol, octanol, etc.). In addition, it is possible for further side reactions to proceed, which can lead, for example, to aldehydes, ketones, carboxylic acids, and/or carboxylic esters as by-products. For example, the acetaldehyde intermediate can form a hemiacetal with the ethanol reactant and dehydrogenation of the hemiacetal can lead to the formation of the ester by-product ethyl acetate. Diethyl ether and ethylene can be formed from the dehydration of ethanol in the presence of an acidic catalyst. The addition of acetaldehyde to butyraldehyde, a crotonaldehyde intermediate, can form 1-hexanol. Butyraldehyde can also react with other intermediates to form 2-ethylbutanol and 2-ethylhexanol. These intermediates can lead to impurities in the butanol product. A crude mixture of the multi-carbon alcohol (e.g., butanol) and impurities can increase the purification needed to recover butanol.

The extent to which these side reactions proceed can, for example, depend on the nature of the starting alcohol, the reaction conditions, and the nature of the catalyst(s). Suppression of the side reactions can lead to the selective production of 1-butanol.

Definitions

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

By "neutral ligands" is meant a molecule fragment that does not react with the reactants or products disclosed herein. Examples of such ligands include, halogens, hydroxyls, carbonyl (C=O), CN, alkyl, alkenyl, cycloalkyl, cycloalkenyl, aryl, and the like.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Methods

Disclosed herein are methods for producing 1-butanol. The methods can comprise, for example, contacting a reactant comprising ethanol with a catalyst system, thereby producing a product comprising 1-butanol. The reactant comprising ethanol can be a fluid (e.g., a gas, a liquid, or combinations thereof).

In some examples, the reactant can be contacted with the catalyst system in a reactor. The reactor may be any suitable reactor. For example, the reactor can comprise a fixed bed reactor, a gas flow reactor, a continuous stirred tank reactor, a fluidized bed reactor, or combinations thereof.

The reactant can be contacted with the catalyst system at a temperature suitable to produce the product. In some examples, the methods described herein can be performed at relatively lower temperatures than conventional Guerbet reactions. In some examples, the reactant can be contacted with the catalyst system at a temperature of 100° C. or more (e.g., 110° C. or more, 120° C. or more, 130° C. or more, 140° C. or more, 150° C. or more, 160° C. or more, 170° C. or more, 180° C. or more, 190° C. or more, 200° C. or more, 220° C. or more, 240° C. or more, 260° C. or more, 280° C. or more, 300° C. or more, 320° C. or more, 340° C. or more, 360° C. or more, 380° C. or more, 400° C. or more, 420° C. or more, 440° C. or more, 460° C. or more, or 480° C. or more). In some examples, the reactant can be contacted with the catalyst system at a temperature of 500° C. or less (e.g., 480° C. or less, 460° C. or less, 440° C. or less, 420° C. or less, 400° C. or less, 380° C. or less, 360° C. or less, 340° C. or less, 320° C. or less, 300° C. or less, 280° C. or less, 260° C. or less, 240° C. or less, 220° C. or less, 200° C. or less, 190° C. or less, 180° C. or less, 170° C. or less, 160° C. or less, 150° C. or less, 140° C. or less, 130° C. or less, 120° C. or less, 110° C. or less, or 100° C. or less). In specific examples, the reaction is performed 200° C., 150° C., 100° C. or less.

The temperature at which the reactant is contacted with the catalyst system can range from any of the minimum values described above to any of the maximum values described above. For example, the reactant can be contacted with the catalyst system at a temperature of from 120° C. to 500° C. (e.g., from 120° C. to 300° C., from 300° C. to 500° C., from 120° C. to 200° C., from 200° C. to 300° C., from 300° C. to 400° C., from 400° C. to 500° C., or from 150° C. to 440° C.). These reactions could be carried out at pressures of 1 atm to 10 atm (e.g., 1, 2, 3, 4, 5, 6, 7, 8, 9 or 10 atm, wherein any of the stated values can form an upper or lower endpoint of a range).

In some examples, the reactant can be contacted with the catalyst system for 0.01 hours or more (e.g., 0.1 hours or more, 0.5 hours or more, 1 hour or more, 2 hours or more, 3 hours or more, 4 hours or more, 5 hours or more, 6 hours or more, 8 hours or more, 10 hours or more, 12 hours or more, 14 hours or more, 16 hours or more, 18 hours or more, 20 hours or more, 22 hours or more, 24 hours or more, 30 hours or more, 36 hours or more, 42 hours or more, 48 hours or more, 60 hours or more, 72 hours or more, 84 hours or more, or 96 hours or more). In some examples, the reactant can be contacted with the catalyst system for 100 hours or less (e.g., 96 hours or less, 84 hours or less, 72 hours or less, 60 hours or less, 48 hours or less, 42 hours or less, 36 hours or less, 30 hours or less, 24 hours or less, 22 hours or less, 20 hours or less, 18 hours or less, 16 hours or less, 14 hours or less, 12 hours or less, 10 hours or less, 8 hours or less, 6 hours or less, 5 hours or less, 4 hours or less, 3 hours or less, 2 hours or less, 1 hour or less, 0.5 hours or less, or 0.1 hours or less).

The time for which the reactant is contacted with the catalyst system can range from any of the minimum values described above to any of the maximum values described above. For example, the reactant can be contacted with the catalyst system for from 0.01 hours to 100 hours (e.g., from 0.01 hours to 48 hours, from 48 hours to 100 hours, from 0.01 hours to 24 hours, from 24 hours to 48 hours, from 48 hours to 72 hours, from 72 hours to 100 hours, from 0.01 hours to 6 hours, or from 1 hour to 72 hours).

In some examples, the ethanol conversion can be 30 mol % or more (e.g., 35 mol % or more, 40 mol % or more, 45 mol % or more, 50 mol % or more, 55 mol % or more, 60 mol % or more, 65 mol % or more, 70 mol % or more, 75 mol % or more, 80 mol % or more, 85 mol % or more, 90 mol % or more, or 95 mol % or more). As used herein, the term "ethanol conversion" refers to the amount of ethanol in the reactant that is converted to a compound other than ethanol in the product, expressed as a percentage based on the amount of ethanol in the reactant. In some examples, the ethanol conversion can be 100% or less (e.g., 95 mol % or less, 90 mol % or less, 85 mol % or less, 80 mol % or less, 75 mol % or less, 70 mol % or less, 65 mol % or less, 60 mol % or less, 55 mol % or less, 50 mol % or less, 45 mol % or less, 40 mol % or less, or 35 mol % or less).

The ethanol conversion can range from any of the minimum values described above to any of the maximum values described above. For example, the ethanol conversion can range from 30 mol % to 100 mol % (e.g., from 30 mol % to 65 mol %, from 65 mol % to 100 mol %, from 30 mol % to 40 mol %, from 40 mol % to 50 mol %, from 50 mol % to 60 mol %, from 60 mol % to 70 mol %, from 70 mol % to 80 mol %, from 80 mol % to 90 mol %, from 90 mol % to 100 mol %, or from 40 mol % to 90 mol %).

In some examples, the 1-butanol selectivity can be 80 mol % or more (e.g., 81 mol % or more, 82 mol % or more, 83 mol % or more, 84 mol % or more, 85 mol % or more, 86 mol % or more, 87 mol % or more, 88 mol % or more, 89 mol % or more, 90 mol % or more, 91 mol % or more, 92 mol % or more, 93 mol % or more, 94 mol % or more, 95 mol % or more, 96 mol % or more, 97 mol % or more, 98 mol % or more, or 99 mol % or more). As used herein, selectivity, as it refers to the formation of 1-butanol, is expressed as the ratio of mols of carbon in the desired 1-butanol product to the mols of carbon in the total product, multiplied by 100 to give a percentage. In some examples, the 1-butanol selectivity can be 100 mol % or less (e.g., 99 mol % or less, 98 mol % or less, 97 mol % or less, 96 mol % or less, 95 mol % or less, 94 mol % or less, 93 mol % or less, 92 mol % or less, 91 mol % or less, 90 mol % or less, 89 mol % or less, 88 mol % or less, 87 mol % or less, 86 mol % or less, 85 mol % or less, 84 mol % or less, 83 mol % or less, 82 mol % or less, or 81 mol % or less).

The 1-butanol selectivity can range from any of the minimum values described above to any of the maximum values described above. For example, the 1-butanol selectivity can range from 80 mol % to 100 mol % (e.g., from 80 mol % to 90 mol %, from 90 mol % to 100 mol %, from 80 mol % to 85 mol %, from 85 mol % to 90 mol %, from 90 mol % to 95 mol %, from 95 mol % to 100 mol %, or from 85 mol % to 95 mol %). In some examples, the selectivity can be greater than 99%.

In some examples, the 1-butanol yield can be 20% or more (e.g., 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more). In some examples, the 1-butanol yield can be 100% or less (e.g., 95% or less, 90% or less, 85% or less, 80% or less, 75% or less, 70% or less, 65% or less, 60% or less, 55% or less, 50% or less, 45% or less, 40% or less, 35% or less, 30% or less, or 25% or less).

The 1-butanol yield can range from any of the minimum values described above to any of the maximum values described above. For example, the 1-butanol yield can range from 20% to 100% (e.g., from 20% to 60%, from 60% to 100%, from 20% to 40%, from 40% to 60%, from 60% to 80%, from 80% to 100%, or from 30% to 90%).

The catalyst system can comprise, for example, an iridium catalyst and a nickel or copper or zinc catalyst. The iridium catalyst can, for example, comprise any iridium catalyst known in the art. In some examples, the iridium catalyst can comprise:

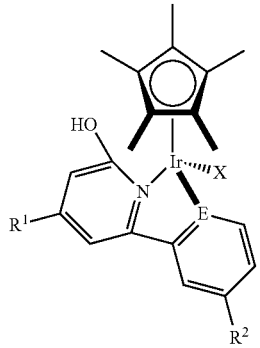

wherein
E is C or N;
X is halogen or other neutral ligand; and
$R^1$ and $R^2$ are independently selected from H, alkyl, alkenyl, cycloalkyl, cycloalkenyl, or aryl. In a specific example, the iridium catalyst can comprise:

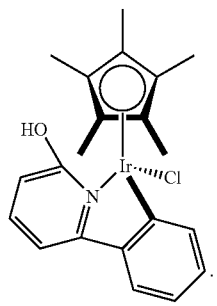

The nickel catalyst can comprise nickel and a sterically bulky ligand. The copper catalyst can comprise copper and a sterically bulky ligand. The zinc catalyst can comprise zinc and a sterically bulky ligand. In some examples, the sterically bulky ligand can reduce or prevent the nickel catalyst from catalyzing the aldol condensation of 1-butanol. In some examples, the sterically bulky ligand can comprise a tripodal ligand. Tripodal ligands are tridentate ligands with $C_3$ symmetry. Examples of tripodal ligands include, for example, scorpionate ligands. Scorpionate ligands are tridentate ligands that can bind to a metal in a fac manner. Examples of scorpionate ligands include, for example, Tp ligands and Tm ligands. Tp ligands are substituted or unsubstituted trispyrazoylborate ligands. For example, the trispyrazoylborate ligand can be substituted on the pyrazoyl rings. In some examples, the sterically bulky ligand can comprise a tris(3,5-dimethyl-1-pyrazolyl)borate ligand. In other examples, the sterically bulky ligand can comprise a tris(3,5-diethyl-1-pyrazolyl)borate, tris(3,5-dipropyl-1-pyrazolyl)borate, tris(3,5-diisopropyl-1-pyrazolyl)borate, tris(3,5-dibutyl-1-pyrazolyl)borate, tris(3,5-di(iso, sec, or tert)butyl-1-pyrazolyl)borate, or tris(1-pyrazolyl)borate ligand. In still other examples, the pyrazolyl moiety of the tris(1-pyrazolyl)borate ligand can be substituted with one or more substituents chosen from hydrogen, alkyl (e.g., isopropyl or tert butyl), cycloalkyl, alkenyl, cycloalkenyl, or aryl. In other examples, the sterically bulky ligand can comprise a substituted aryl, e.g., a di or tri alkyl substituted aryl.

In some examples, the nickel catalyst can comprise:

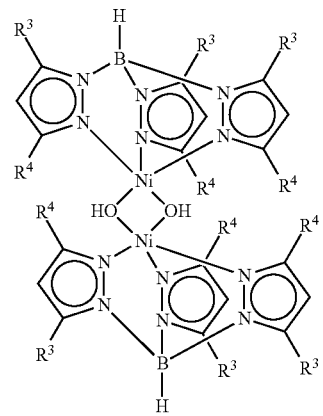

wherein each $R^3$ and $R^4$ are independently selected from H, alkyl, alkenyl, cycloalkyl, cycloalkenyl, or aryl. In a specific example, the nickel catalyst can comprise

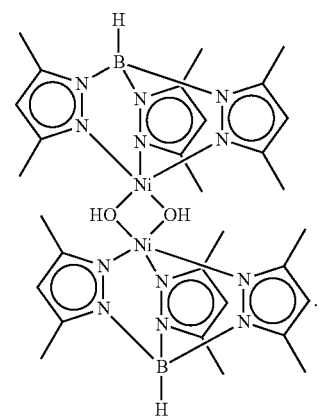

In a specific example, the copper catalyst can comprise:

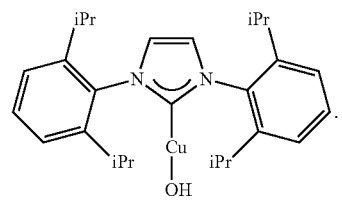

In some examples, the catalyst can comprise:

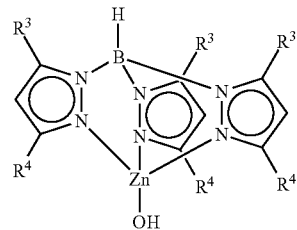

wherein each $R^3$ and $R^4$ are independently selected from H, alkyl, alkenyl, cycloalkyl, cycloalkenyl, or aryl. In specific examples, each $R^3$ and $R^4$ are independently selected from methyl, ethyl, propyl (e.g., iso-propyl), and butyl (e.g., sec-butyl or tert-buty).

In a specific example, the nickel, copper, or zinc catalyst can comprise:

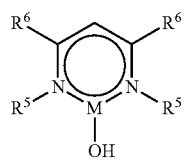

wherein M is Ni, Cu, or Zn; and $R^5$ and $R^6$ are independently selected from H, alkyl, alkenyl, cycloalkyl, cycloalkenyl, or aryl. In specific examples, each $R^5$ and $R^6$ are independently selected from methyl, ethyl, propyl (e.g., iso-propyl), and butyl (e.g., sec-butyl or tert-buty). In specific examples, $R^5$ and/or $R^6$ are independently selected from di- or tri-alkyl substituted aryl, e.g., aryl with two or three methyl, ethyl, propyl (e.g., iso-propyl), or butyl (e.g., sec-butyl or tert-buty) groups. Examples of these catalyst are disclosed in Dai, *Chem. Commun.* 2001, 1998-1999 (copper); Yao et al., *Angew. Chem. Int. Ed.* 2008, 47, 7110-7113 (nickel); Gondzik et al., *Chem. Commun.* 2014, 1189 (zinc).

In some examples, the methods described herein provide an improved process for dimerizing ethanol in the manner of a Guerbet reaction to produce 1-butanol. In some examples, for the Guerbet process for the conversion of ethanol to 1-butanol, the iridium catalyst can catalyze the dehydrogenation of ethanol to acetaldehyde and the hydrogenation of butenal to 1-butanol, while the nickel catalyst can catalyze the aldol condensation of acetaldehyde to produce butenal.

In still further examples, disclosed herein are methods or preparing sec butanol from methanol and ethanol or propanol and methanol. In still other methods, disclosed herein are methods of preparing 2-ethylhexanol from ethanol. These reactions are shown below.

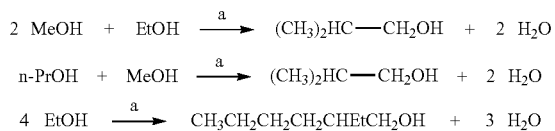

where "a" is catalyst system as disclosed herein.

Catalyst Systems

Also disclosed herein are catalyst systems comprising an iridium catalyst and a nickel, copper, or zinc catalyst, wherein the nickel, copper, or zinc catalyst comprises nickel, copper, and/or zinc and a sterically bulky ligand. The nickel, copper, and zinc catalyst are hindered bases.

The iridium catalyst can, for example, comprise any iridium catalyst known in the art. In some examples, the iridium catalyst can comprise:

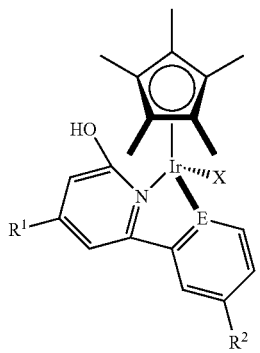

wherein

E is C or N;

X is halogen or other neutral ligand; and $R^1$ and $R^2$ are independently selected from H, alkyl, alkenyl, cycloalkyl, cycloalkenyl, or aryl. In a specific example, the iridium catalyst can comprise:

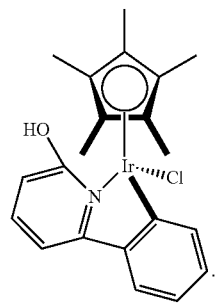

The nickel, copper, and/or zinc catalyst is a hindered base and therefore has one or more sterically bulky ligands. In some examples, the sterically bulky ligand can comprise a tripodal ligand. Tripodal ligands are tri- and tetradentate ligands with $C_3$ symmetry. Examples of tripodal ligands include, for example, scorpionate ligands. Scorpionate ligands are tridentate ligands that can bind to a metal in a fac manner. Examples of scorpinate ligands include, for example, $T_p$ ligands and $T_m$ ligands. $T_p$ ligands are substituted or unsubstituted trispyrazoylborate ligands. For example, the trispyrazoylborate ligand can be substituted on the pyrazoyl rings. In some examples, the sterically bulky ligand can comprise a tris(3,5-dimethyl-1-pyrazolyl)borate ligand. In other examples, the sterically bulky ligand can comprise a tris(3,5-diethyl-1-pyrazolyl)borate, tris(3,5-dipropyl-1-pyrazolyl)borate, tris(3,5-diisopropyl-1-pyrazolyl)borate, tris(3,5-dibutyl-1-pyrazolyl)borate, tris(3,5-di(iso, sec, or tert)buty-1-pyrazolyl)borate, or tris(1-pyrazolyl)borate ligand. In still other examples, the pyrazolyl moiety of the tris(1-pyrazolyl)borate ligand can be substituted with one or more substituents chosen from hydrogen, halogen, alkyl, cycloalkyl, alkenyl, cycloalkenyl, or aryl. In some examples, the nickel catalyst can comprise:

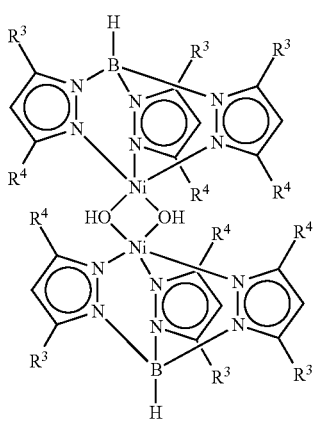

wherein each $R^3$ and $R^4$ are independently selected from H, alkyl, alkenyl, cycloalkyl, cycloalkenyl, or aryl. In a specific example, the nickel catalyst can comprise:

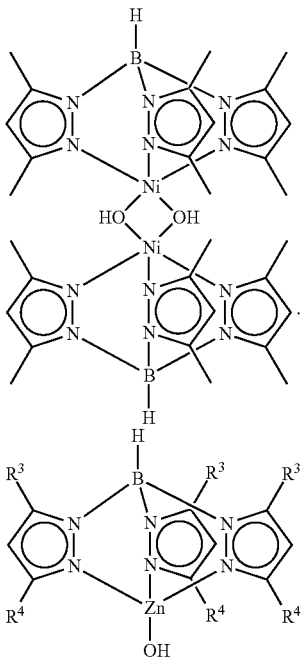

wherein each $R^3$ and $R^4$ are independently selected from H, alkyl, alkenyl, cycloalkyl, cycloalkenyl, or aryl. In specific examples, each $R^3$ and $R^4$ are independently selected from methyl, ethyl, propyl (e.g., iso-propyl), and butyl (e.g., sec-butyl or tert-buty). In a specific example, the nickel catalyst is a Tp complex or 1,3-diketimine ligand (nacnac) of nickel.

In a specific example, the nickel, copper, or zinc catalyst can comprise:

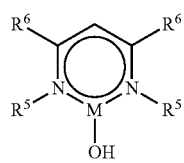

wherein M is Ni, Cu, or Zn; and $R^5$ and $R^6$ are independently selected from H, alkyl, alkenyl, cycloalkyl, cycloalkenyl, or aryl. In specific examples, each $R^5$ and $R^6$ are independently selected from methyl, ethyl, propyl (e.g., iso-propyl), and butyl (e.g., sec-butyl or tert-buty). In specific examples, $R^5$ and/or $R^6$ are independently selected from di- or tri-alkyl substituted aryl, e.g., aryl with two or three methyl, ethyl, propyl (e.g., iso-propyl), or butyl (e.g., sec-butyl or tert-buty) groups.

In a specific example, the copper catalyst can comprise:

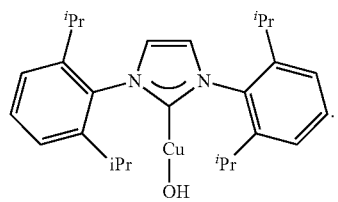

In other examples, the copper catalyst is a Tp complex or 1,3-diketimine ligand (nacnac) of copper.

In a specific example, the zinc catalyst is a Tp complex or 1,3-diketimine ligand (nacnac) of zinc.

EXAMPLES

The following examples are set forth below to illustrate the compositions, methods, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Unless otherwise noted, all the organometallic compounds were prepared and handled under a nitrogen atmosphere using standard Schlenk and glovebox techniques. Dry and oxygen-free solvents such as THF, p-xylene, toluene, and $CH_2Cl_2$ were vacuum transferred from either a purple solution of Na/benzophenone ketyl or $CaH_2$ and stored over 4 Å molecular sieves. Anhydrous ethanol (200 proof, >99.5% assay) was purchased from Sigma Aldrich and stored over 4 Å molecular sieves. $^1H$ and $^{13}C$ NMR spectra were recorded on Bruker Avance-400 MHz and 500 MHz spectrometers and chemical shift values were referenced internally to the residual solvent resonances. Infrared spectra were recorded in the solid state on a Thermo Scientific Nicolet 4700 FT-IR spectrometer equipped with smart orbit diamond attenuated total reflectance (ATR) accessory. Elemental analysis was performed by the CENTC Elemental Analysis Facility at the University of Rochester using a Perkin Elmer 2400 Series II elemental analyzer in CHN mode. KTp', (2-OH-6-henyl)pyridine (Tp'=tris(3,5-dimethyl-pyrazolylborate), and IPr.HCl (IPr=1,3-bis(2,6-di-isopropylphenyl)-1,3-dihydro-2H-imidazol-2-ylidene] were purchased from Strem Chemicals Co., Alfa Aesar, and Sigma Aldrich, respectively. KTp' was further recrystallized from ethanol prior to use. Preparation of Ir (Fujita, K.-I.; et al., *Org. Lett.* 2011, 13, 2278-2281), [Tp'Ni(p-OH)]$_2$ (Ni2) dimer (Hikichi, S.; et al., *Chem. Eur. J.* 2001, 7, 5012-5028), (IPr)CuOH (Cu) (Fortman, G. C.; et al., *Organometallics* 2010, 29, 3966-3972), and (IPr)CuCl (Citadelle, C. A.; et al., *Dalton Trans.* 2010, 4489-4491) have been previously reported in the literature. Compounds shown in Table 1 are synthesized according to the literature procedures (Fujita, K.-I.; et al., *Org. Lett.* 2007, 9, 109-111. (b) Zhang, J., et al., *J. Am. Chem. Soc.* 2005, 127, 10840-10841. (c) Gnanaprakasam, B., et al., *Angew. Chem. Int. Ed.* 2010, 49, 1468-1471). All samples from the catalytic reactions were analyzed by a Shimadzu QP2010 GC-MS instrument (Supelco SPB1701, 60 m×0.25 mm, thickness 0.25 μm). Method used: starting oven temperature is 50° C. (hold for 5 min), then heated to 260° C. at 15° C./min (hold for 20 min); column pressure: 24.5 psi, total flow: 112 mL/min, column flow: 1.05 mL/min, split ratio: 100, linear velocity: 21.2 cm/sec.

Example 1: General Procedure for the Ir-Catalyzed Guerbet Reaction of Ethanol in the Presence of Common Inorganic Bases In a catalytic run, an oven-dried Schlenk tube was loaded with Ir (5 mg, 10 μmol) and a base (500 μmol) inside a glovebox. Ethanol (5 mmol-33 mmol) was added to this reaction mixture under a nitrogen atmosphere via a syringe and the resulting solution was heated to 150° C. for a specific amount of time using an aluminum heating block. After the reaction run time, the Schlenk tube was first allowed to cool to room temperature and then kept in an ice-water bath for 30 min to prevent the loss of ethanol due to evaporation. After carefully opening the valve, an aliquot was quickly withdrawn by a pipette, filtered through a very short plug of Celite, and the filtrate was analyzed by GC-MS (120 μL sample, 43 μL tridecane as internal standard, and 3 mL THF), showing mixed products (Scheme 3).

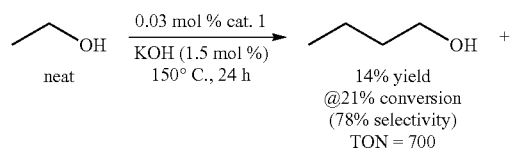

Scheme 3.
Results of Guerbet process for the conversion of ethanol to butanol using an iridium compound and KOH as catalysts (Table 1, entry 6).

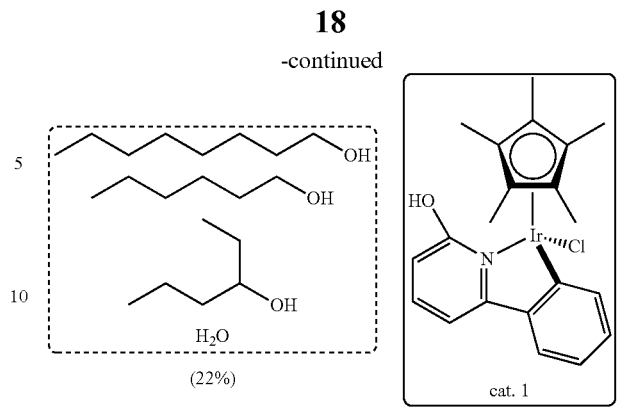

Example 2: Guerbet Reaction of Ethanol with Other Transition-Metal Catalysts In a typical catalytic run, an oven-dried Schlenk tube was loaded with a transition-metal catalyst and a base. Ethanol was added to this reaction mixture under a nitrogen atmosphere via a syringe and the resulting solution was heated to 150° C. for a specific amount of time using an aluminum heating block. After the reaction run time, the Schlenk tube was first allowed to cool to room temperature and then kept in an ice-water bath to prevent the loss of ethanol due to evaporation. After carefully opening the valve, an aliquot was quickly withdrawn by a syringe, filtered through a very short plug of Celite, and the filtrate was analyzed by GC-MS. These results are summarized in Table 1.

Example 3: General Procedure for the Conversion of Ethanol to n-Butanol Through Tandem Catalysis An oven-dried Schlenk tube was charged with Ir (5 mg, 0.010 mmol) and either Ni$_2$ (194 mg, 0.250 mmol) or Cu (235 mg, 0.500 mmol) inside a glovebox. Ethanol (0.291 mL, 5 mmol) was added to this reaction mixture under a nitrogen atmosphere and the resulting suspension was heated to 150° C. for 24 h. The Schlenk tube was first allowed to cool to room temperature and then kept in an ice-water bath for 30 min to prevent the loss of ethanol due to evaporation. After carefully opening the valve, an aliquot was quickly withdrawn by a syringe, filtered through a very short plug of Celite, and the filtrate was analyzed by GC-MS (120 μL of sample, 43 μL of tridecane as an internal standard, and 3 mL of THF).

When the Guerbet reaction of neat ethanol was performed at 150° C. for 24 h in the presence of both Ir and Ni$_2$ (a relative ratio of 1:25), n-butanol was produced as the sole Guerbet product. Longer-chain Guerbet products, commonly observed in other cases, were not observed in this reaction which makes this tandem catalytic process unique (analyzed by gas chromatography). 37% of ethanol was converted to n-butanol (34% GC yield) in this process with a selectivity as high as >99% (Table 1, entry 14). Under the same conditions, the copper-containing base also produced n-butanol with a high yield and selectivity at 32% ethanol conversion (Table 1, entry 15). This tandem catalytic process represents the best activity observed to date in the Guerbet reaction of ethanol.

Example 4: Nickel and Copper-Catalyzed Aldol Reactions

A flame-dried thick-walled Schlenk tube was charged with either $Ni_2$ (10 mg, 12.5 μmol) or Cu (12 mg, 25 μmol), an aldehyde substrate (2.5 mmol), and 1 mL of THF. The resulting solution was heated to 150° C. for 24 h and the sample was analyzed by gas chromatography after performing a similar work-up procedure to that mentioned above. Crotonaldehyde (m/z=70) was formed as the sole aldol product when acetaldehyde was used as the reactant. While no further aldol reaction occurred with crotonaldehyde, 1-butanal produced traces of the $C_8$ coupling product. These reactions were performed behind a protective glass shield inside the hood.

TABLE 1

Guerbet Reaction of Ethanol with Transition-Metal Catalysts.

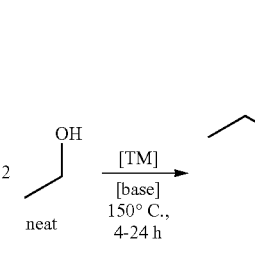

| entry | catalyst (mol %) | base | % conv. (% yield)[a] | selectivity (%)[b] | TON[c] |
|---|---|---|---|---|---|
| 1 | Ir (0.2) | NaOEt | 6 (4) | 91 | 30 |
| 2 | Ir (0.2) | KO$^t$Bu | 23 (12) | 61 | 115 |
| 3 | Ir (0.2) | KOH | 31 (26) | 83 | 155 |
| 4[d] | Ir (0.2) | KOH | 40 (33) | 77 | 200 |
| 5[d] | Ir (0.1) | KOH | 34 (28) | 80 | 340 |
| 6[d] | Ir (0.03) | KOH | 21 (14) | 78 | 700 |
| 7[d,e] | Ir (0.2) | – | 21 | – | 105 |
| 8 | 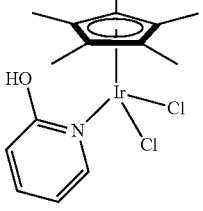 (0.2) | KOH | 19 (9) | 43 | 95 |
| 9 | 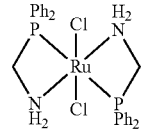 (0.2) | KOH | 21 (7) | 37 | 105 |
| 10[f] | $RuCl_2(PPh_3)_3$ (1.0) | KOH | 45 (6) | 84 | 45 |
| 11[f] | (see structure) (1.0) | KOH | 73 (9) | 72 | 73 |

TABLE 1-continued

Guerbet Reaction of Ethanol with Transition-Metal Catalysts.

$$2 \text{ CH}_3\text{CH}_2\text{OH} \xrightarrow[\text{150° C., 4-24 h}]{\text{[TM], [base], neat}} \text{CH}_3\text{CH}_2\text{CH}_2\text{CH}_2\text{OH} + \text{H}_2\text{O}$$

[Ir catalyst structure shown] ≡ Ir

| entry | catalyst (mol %) | base | % conv. (% yield)[a] | selectivity (%)[b] | TON[c] |
|---|---|---|---|---|---|
| 12[e] | Ru(CNN) P^tBu_2/NEt_2/Cl/CO/H (1.0) | KOH | 46 (–) | – | 46 |
| 13[f] | Ru(CNN) P^tBu_2/P^tBu_2/Cl/CO/H (1.0) | KOH | 20 (4) | 52 | 20 |
| 14 | Ir (0.2)[g] | Ni_2[h] | 37 (34) | >99 | 185 |
| 15 | Ir (0.2)[g] | Cu[h] | 32 (28) | >99 | 160 |

[a]Conversion of ethanol to Guerbet products, with the yield of n-butanol in parentheses (determined by gas chromatography). [b]Selectivity of n-butanol in the liquid fraction (determined by gas chromatography). [c]Turnover number (TON) is calculated based on moles of ethanol converted to Guerbet products per mole of iridium. [d]Run for 24 h. [e]The only product is ethyl acetate. [f]12 h, THF solvent. [g][Ir] = 0.034M. [h][Ni_2] = 0.85M or [Cu] = 1.7M.

The nickel and copper catalyzed reaction of acetaldehyde were investigated and the results were compared to the same reaction catalyzed by KOH. Consistent with Wass's result with NaOEt (Dowson, G. R. M.; et al., *Angew. Chem. Int. Ed.* 2013, 52, 9005-9008; Wingad, R. L.; et al., *ACS Catal.* 2015, 5, 5822-5826), KOH-catalyzed aldol condensation of acetaldehyde was found to produce the desired $C_4$ coupling product, crotonaldehyde, with only 23% selectivity after 1 day at 150° C. In marked contrast, the same reaction catalyzed by either $Ni_2$ or Cu generated crotonaldehyde as the exclusive coupling product under the same conditions (Scheme 4).

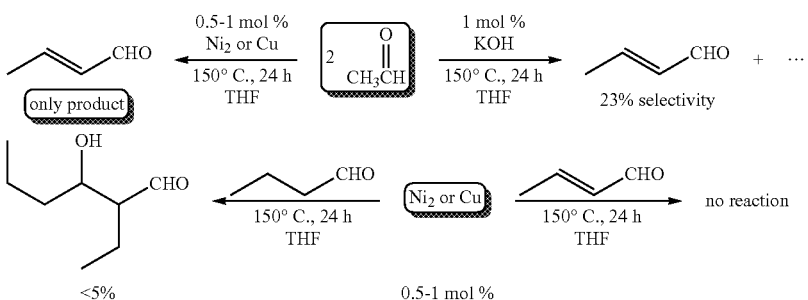

Scheme 4: Nickel and Copper Catalyzed Aldol Reactions

The remarkable selectivity observed in the aldol reaction of acetaldehyde with these bulky transition-metal hydroxide complexes is unprecedented in the literature and provides a strategy to chemically discriminate for coupling between two small ($C_2$) aldehyde molecules. To further test this hypothesis, catalytic aldol coupling of 1-butanal ($C_4$) was performed in the presence of $Ni_2$ (1 mol %), and only traces of $C_8$ product were detected by gas chromatography (Scheme 4). Furthermore, nickel-catalyzed aldol reaction of crotonaldehyde did not generate any $C_8$ or longer-chain products. A similar trend in reactivity was observed with Cu, however products were formed with slightly lower yields as the thermal stability of Cu was found to be lower than the $Ni_2$ complex. Nonetheless, these results indicate that the steric crowding at the metal center plays a key role in determining the aldol-product distribution, and this feature can be fine-tuned to dictate the outcome of the reaction.

Example 5: Control Experiments

In order to determine if $Ni_2$ or Cu is involved in the dehydrogenation and hydrogenation steps of the Guerbet process, dehydrogenation of ethanol and hydrogenation (with 1 atm $H_2$) of crotonaldehyde were carried out using either $Ni_2$ or Cu as catalysts (Scheme 5).

Scheme 5: Control Experiments

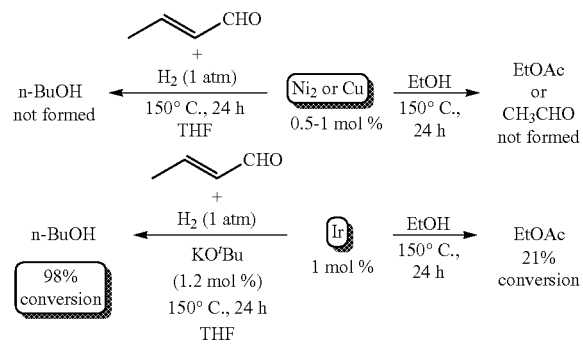

(a) Nickel and Copper-Catalyzed Dehydrogenation of Ethanol:

Ethanol solutions (0.146 mL, 2.5 mmol) of $Ni_2$ (10 mg, 12.5 µmol) or Cu (12 mg, 25 µmol) were heated to 150° C. for 24 h and the samples were analyzed by gas chromatography. The formation of ethyl acetate, acetaldehyde, or crotonaldehyde were not detected by GC.

(b) Nickel and Copper-Catalyzed Hydrogenation of Crotonaldehyde:

A THF solution containing $Ni_2$ (10 mg, 12.5 µmol) or Cu (12 mg, 25 µmol) and crotonaldehyde (0.207 mL, 2.5 mmol) was subjected to 1 atm of $H_2$ pressure in a steel Parr pressure reactor and heated to 150° C. for 24 h. After that the residual hydrogen pressure was released and the samples were analyzed by gas chromatography. The formation of either n-butanol or other partially reduced species were not detected by GC.

(c) Ir-Catalyzed Dehydrogenation of Ethanol in the Absence of a Base:

An ethanol solution (0.146 mL, 2.5 mmol) of Ir (12 mg, 25 µmol) was heated to 150° C. for 24 h and the sample was analyzed by gas chromatography. 21% of ethyl acetate was formed in this reaction. No longer-chain Guerbet alcohols including n-butanol were formed.

(d) Ir-Catalyzed Hydrogenation of Crotonaldehyde:

A THF solution containing Ir (12 mg, 25 µmol), KOtBu (3 mg, 30 µmol), and crotonaldehyde (0.207 mL, 2.5 mmol) was subjected to 1 atm of $H_2$ pressure in a steel Parr pressure reactor and heated to 150° C. for 24 h. The residual hydrogen pressure was released and the sample was analyzed by gas chromatography. Quantitative conversion of crotonaldehyde to n-butanol was observed suggesting that the iridium catalyst is capable of fully hydrogenating a α,β-unsaturated aldehyde (both C═C and C═O bonds) under these conditions. No product arising from the partial hydrogenation was detected in this reaction.

None of the above control reactions resulted in butanol formation, suggesting that these metal hydroxides only assist in the aldol condensation step in the Guerbet reaction sequence. On the other hand, Ir catalyzed dehydrogenation of ethanol produced ethyl acetate as the only product (21%, entry 7, Table 1). Catalytic hydrogenation (1 atm $H_2$) of crotonaldehyde with either a mixture Ir and KOtBu (1:1.2) or the related Cp*Ir[(2-OH-6-phenyl)-pyridine](H) (Fujita, K.-L.; et al., Org. Lett. 2011, 13, 2278-2281) complex produced the fully hydrogenated product n-butanol quantitatively (Scheme 5). These control studies imply that while Ir catalyst participates in the dehydrogenation and hydrogenation steps, $Ni_2$ or Cu aids in the aldol condensation step involved in the Guerbet reaction. However, these control experiments do not rule out the mechanism in which the iridium catalyst also assists in the aldol step during the Guerbet catalysis.

Example 6: Stoichiometric Reaction Between the Iridium and Copper Complexes, Followed by the Addition of Ethanol Acceptorless dehydrogenation of ethanol is one of the most challenging steps involved in the Guerbet process. Often high temperatures are required to favor the equilibrium toward the product, acetaldehyde (Carlini, C.; et al., J. Mol. Catal. A: Chem. 2003, 200, 137-146; Furukawa, J.; et al., J. Polym. Sci. 1959, 36, 546; Degering, E. F.; et al., J. Polym. Sci. 1951, 7, 653-656). If this step could be performed effectively at a lower temperature, the overall Guerbet process could be carried out under much milder conditions. To explore this possibility, we investigated this key step separately by NMR spectroscopy. As $Ni_2$ is a paramagnetic complex and it causes NMR signal-broadening, we used the diamagnetic Cu complex for these NMR studies.

In a glovebox, a J. Young NMR tube was charged with Ir (13 mg, 25 µmol), Cu (12 mg, 25 µmol), and ~0.7 mL of $CD_2Cl_2$. An instantaneous reaction occurred as the initial yellow color of Ir changed to deep red and the reaction was monitored by $^1H$ NMR spectroscopy. The characteristic OH resonance (δ 8.07, singlet) of Ir was disappeared upon addition of the Cu complex and therefore this new iridium species was tentatively assigned to be the pyridone form (Ir'). On the other hand, the characteristic Cu—OH resonance (δ −1.93, singlet) of the Cu complex was no longer visible in the $^1H$ NMR spectrum and the formation of (IPr)CuCl complex was observed. The methyl resonance of the Cp* moiety in Ir was also shifted upfield from δ 1.62 to δ 1.41. To this reaction mixture, anhydrous ethanol was added (3 µL, 50 µmol) via a syringe and the progress of the reaction was monitored by $^1H$ NMR spectroscopy. At room temperature, no reaction occurred as the resonances for both the iridium species and ethanol remained unchanged. When heated to 100° C., the deep red color of the solution faded gradually and changed to orange within an hour. A $^1H$ NMR spectrum (THF-$d_8$) recorded at this point showed the presence of both $CH_3CHO$ (δ 9.66, singlet, $CH_3CHO$) and an iridium hydride species, (Cp*Ir[(2-OH-6-Ph)py](H), δ −15.27, singlet, IrH) (Scheme 6). The identification of the iridium hydride species was verified by independently synthesizing an authentic sample (Fujita, K.-I.; et al., Org. Lett. 2011, 13, 2278-2281).

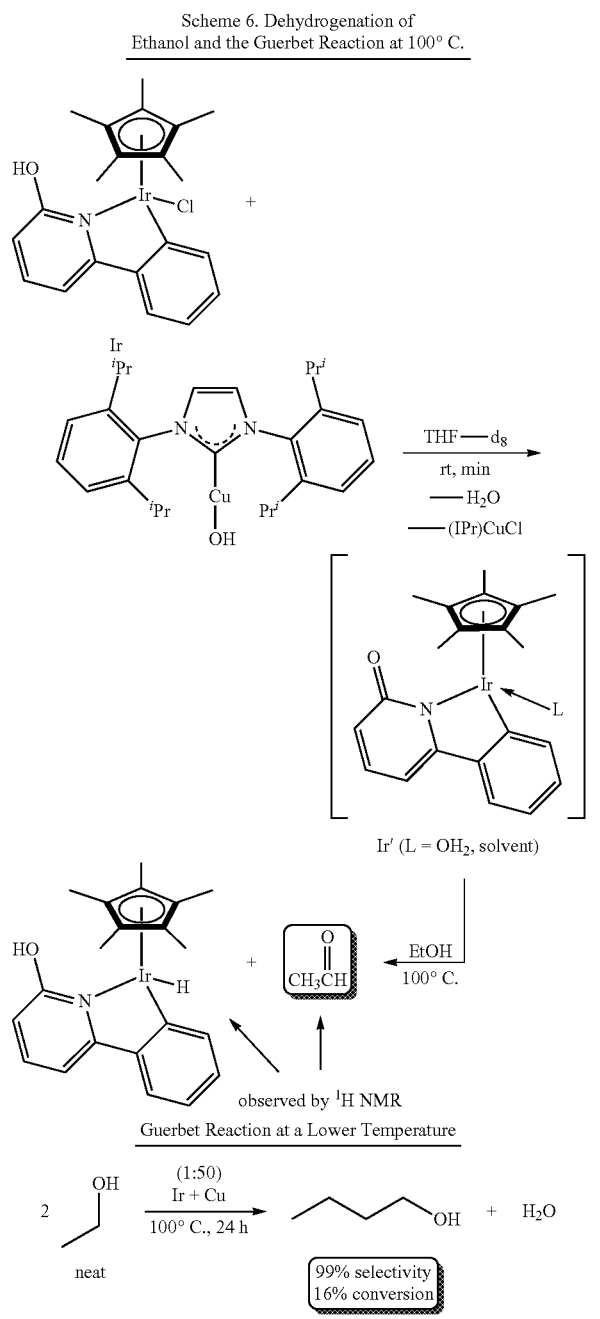

Scheme 6. Dehydrogenation of Ethanol and the Guerbet Reaction at 100° C.

The results of these $^1$H NMR studies indicate that it is possible to perform the dehydrogenation of ethanol, and therefore the Guerbet process, at temperatures as low as 100° C. Ethanol could be successfully converted to n-butanol even at 100° C. with >99% selectivity.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for producing 1-butanol, comprising: contacting a reactant comprising ethanol with a catalyst system, thereby producing a product comprising 1-butanol, wherein the catalyst system comprises:
   an iridium catalyst; and
   a nickel catalyst comprising nickel, hydroxide, and a ligand, a copper catalyst comprising copper, hydroxide, and a ligand, or a zinc catalyst comprising zinc, hydroxide, and a ligand.

2. The method of claim 1, wherein the ligand comprises a tripodal ligand.

3. The method of claim 1, wherein the ligand comprises a scorpionate ligand.

4. The method of claim 1, wherein the ligand comprises a substituted or unsubstituted trispyrazoylborate ligand.

5. The method of claim 1, wherein the ligand comprises a tris(3,5-dimethyl-1-pyrazolyl)borate, tris(3,5-diethyl-1-pyrazolyl)borate, tris(3,5-dipropyl-1-pyrazolyl)borate, tris(3,5-diisopropyl-1-pyrazolyl)borate, tris(3,5-dibutyl-1-pyrazolyl)borate, tris(3,5-di(iso, sec, or tert)butyl-1-pyrazolyl)borate, or tris(1-pyrazolyl)borate ligand substituted with one or more substituents chosen from hydrogen, halogen, alkyl, alkenyl, cycloalkyl, cycloalkenyl, or aryl ligand.

6. The method of claim 1, wherein the catalyst system comprises the nickel catalyst and it comprises:

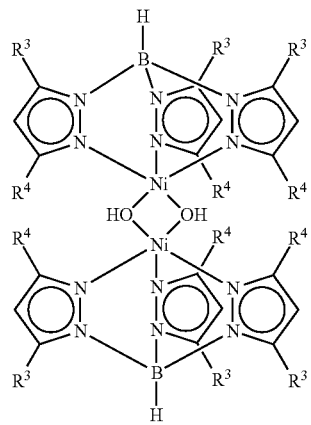

wherein each $R^3$ and $R^4$ are independently selected from H, alkyl, alkenyl, cycloalkyl, cycloalkenyl, or aryl.

7. The method of claim 6, wherein the catalyst comprises:

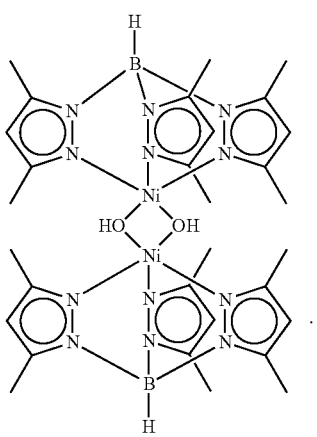

8. The method of claim 1, wherein catalyst system comprise the copper catalyst and it comprises:

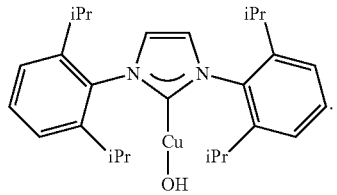

9. The method of claim 1, wherein nickel, copper, and zinc catalyst have the formula:

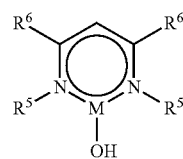

wherein M is Ni, Cu, or Zn; and $R^5$ and $R^6$ are independently selected from H, alkyl, alkenyl, cycloalkyl, cycloalkenyl, and aryl.

10. The method of claim 9, wherein each $R^5$ and $R^6$ are independently selected from methyl, ethyl, iso-propyl, sec-butyl, and tert-butyl.

11. The method of claim 9, wherein $R^5$ and/or $R^6$ are independently selected from di- or tri-alkyl substituted aryl.

12. The method of claim 1, wherein the iridium catalyst comprises:

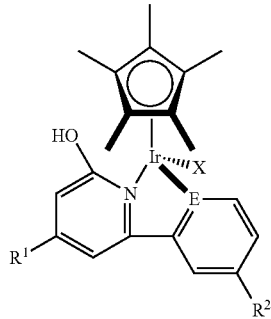

wherein

E is C or N;

X is halogen or other neutral ligand; and $R^1$ and $R^2$ are independently selected from H, alkyl, alkenyl, cycloalkyl, cycloalkenyl, or aryl.

13. The method of claim 1, wherein the iridium catalyst comprises:

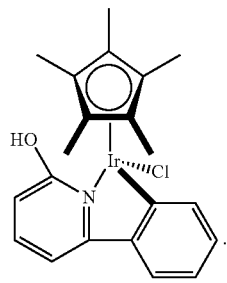

14. The method of claim 1, wherein the reactant is contacted with the catalyst system at a temperature of from 100° C. to 500° C., from 0.01 hour to 100 hours, at from 1 atm to 10 atm.

15. The method of claim 1, wherein the 1-butanol selectivity is 80% or more and the 1-butanol yield is 20% or more.

16. A catalyst system for producing 1-butanol, comprising:

an iridium catalyst; and a nickel catalyst comprising nickel, hydroxide, and a ligand, a copper catalyst comprising copper, hydroxide, and a ligand, or a zinc catalyst comprising zinc, hydroxide, and a ligand.

17. The catalyst system of claim 16, wherein the ligand comprises a tripodal ligand.

18. The catalyst system of claim 16, wherein the ligand comprises a scorpionate ligand.

19. The catalyst system of claim 16, wherein the ligand comprises a substituted or unsubstituted trispyrazoylborate ligand.

20. The catalyst system of claim 16, wherein the ligand comprises a tris(3,5-dimethyl-1-pyrazolyl)borate, tris(3,5-diethyl-1-pyrazolyl)borate, tris(3,5-dipropyl-1-pyrazolyl)borate, tris(3,5-diisopropyl-1-pyrazolyl)borate, tris(3,5-dibutyl-1-pyrazolyl)borate, tris(3,5-di(iso, sec, or tert)butyl-1-pyrazolyl)borate, or tris(1-pyrazolyl)borate ligand substituted with one or more substituents chosen from hydrogen, halogen, alkyl, alkenyl, cycloalkyl, cycloalkenyl, or aryl ligand.

21. The catalyst system of claim 16, wherein the system comprises the nickel catalyst and the nickel catalyst comprises:

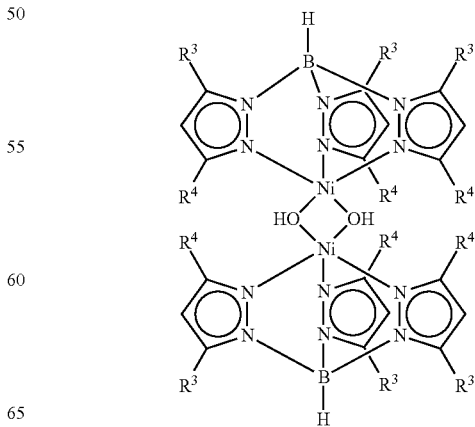

wherein each $R^3$ and $R^4$ are independently selected from H, alkyl, alkenyl, cycloalkyl, cycloalkenyl, or aryl.

22. The catalyst system of claim 21, wherein the nickel catalyst comprises:

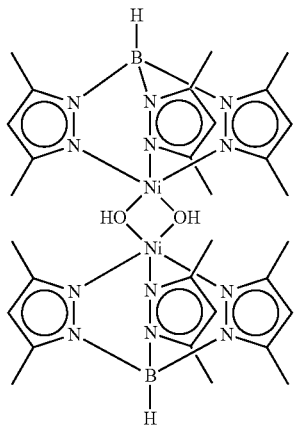

23. The catalyst system of claim 16, wherein the system comprises the copper catalyst and the copper catalyst comprises:

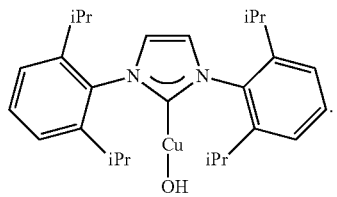

24. The catalyst system of claim 16, wherein nickel, copper, and zinc catalyst have the formula:

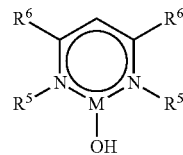

wherein M is Ni, Cu, or Zn; and $R^5$ and $R^6$ are independently selected from H, alkyl, alkenyl, cycloalkyl, cycloalkenyl, and aryl.

25. The catalyst system of claim 24, wherein each $R^5$ and $R^6$ are independently selected from methyl, ethyl, iso-propyl, sec-butyl, and tert-butyl.

26. The catalyst system of claim 24, wherein $R^5$ and/or $R^6$ are independently selected from di- or tri-alkyl substituted aryl.

27. The catalyst system of claim 16, wherein the iridium catalyst comprises:

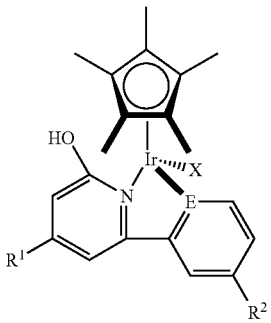

wherein
E is C or N;
X is halogen or other neutral ligand; and
$R^1$ and $R^2$ are independently selected from H, alkyl, alkenyl, cycloalkyl, cycloalkenyl, or aryl.

28. The catalyst system of claim 16, wherein the iridium catalyst comprises:

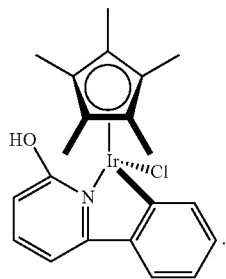

* * * * *